United States Patent [19]
Attridge et al.

[11] Patent Number: 5,192,502
[45] Date of Patent: Mar. 9, 1993

[54] DEVICES FOR USE IN CHEMICAL TEST PROCEDURES

[75] Inventors: John W. Attridge, Weybridge; Alan M. Smith, Altrincham, both of United Kingdom

[73] Assignee: Ares-Serono Research & Development Limited Partnership, Boston, Mass.

[21] Appl. No.: 623,734

[22] PCT Filed: May 17, 1990

[86] PCT No.: PCT/GB90/00764
§ 371 Date: Dec. 13, 1990
§ 102(e) Date: Dec. 13, 1990

[87] PCT Pub. No.: WO90/14590
PCT Pub. Date: Nov. 29, 1990

[30] Foreign Application Priority Data
May 18, 1989 [GB] United Kingdom ............... 8911462

[51] Int. Cl.⁵ .......................................... G01N 21/01
[52] U.S. Cl. ..................................... 422/57; 356/246; 385/12; 422/82.11
[58] Field of Search ................... 422/86.06–86.08, 422/82.11, 57–58; 436/527, 531; 385/12, 13; 250/459.1; 356/246

[56] References Cited
U.S. PATENT DOCUMENTS
4,824,789  4/1989  Yafuso et al. .................... 436/68
4,978,503  12/1990  Shanks et al. .................... 422/58

FOREIGN PATENT DOCUMENTS
0103426  3/1984  European Pat. Off. .
0170376  2/1986  European Pat. Off. .
0171148  2/1986  European Pat. Off. .

*Primary Examiner*—Jill A. Johnston
*Attorney, Agent, or Firm*—Ostrolenk, Faber, Gerb & Soffen

[57] ABSTRACT

The invention relates to a device for use in methods of assay, for example those involving fluorescent moieties. The device possesses a cavity or cavities into which the sample liquid may be drawn by capillary action. Each cavity is formed from two transparent solid plates (35,36): one (36) is adapted to act as a waveguide and carries a suitable immobilized reagent on its surface within the cavity; the other (35) carries on its external surface and optionally also on part only of its internal surface a layer of light-absorbing material (37). The invention also relates to a method of manufacturing devices according to the invention, and to a method of assaying for a ligand in a sample using a device according to the invention.

5 Claims, 6 Drawing Sheets

Standard Curve for Cells with no Opaque layer

DEVICES FOR USE IN CHEMICAL TEST PROCEDURES

This invention relates to devices for use in chemical, biochemical or clinical test procedures, to processes for their manufacture, and to methods of using the devices.

More particularly, the invention relates to devices suitable for use in specific binding assays, among which an important group is constituted by immunoassays.

Various analytical devices for handling and metering small volumes of test samples have been described in the prior art. In particular, EP-A-171148 describes capillary fill cell devices which can be conveniently manufactured and which are suitable for specific binding assays using very small liquid samples. These devices possess a cavity or cavities each having a dimension small enough to enable sample liquid to be drawn into the cavity by capillary action, wherein a surface of the cavity carries an immobilised reagent appropriate to the test to be carried out in the device, and wherein said surface is a surface of a transparent solid plate adapted to act as a light-transmissive waveguide and forming a wall of the cavity, said plate having an edge which is substantially optically smooth ("the optical edge") and transverse, e.g. at some transverse angle, but most preferably perpendicular, to the plane of the plate. Such devices enable convenient sample collection and optical analysis in situ of the products of reaction of the sample with the said immobilised reagent. The waveguide plate should be transparent to radiation of the wavelength intended to be employed, e.g. infrared, visible and/or ultraviolet light, and one method of using a device as described in EP-A-171148 is to arrange for a fluorescent material to become bound to the immobilised reagent to an extent which will vary depending on the assay and the sample material being assayed and then to carry out optical measurement of the resulting bound fluorescent material.

EP-A-171148 discloses the possibility that for some forms of assay it may be appropriate for the wall of the capillary cavity opposite to the reagent-bearing waveguide surface to be made of a light-absorbing, opaque or reflective material, i.e. for the device to have the structure depicted in FIG. 1, described in more detail later.

The difference in angular distributions of fluorescence arising from fluorophores in the analyte solution and fluorophores bound to the waveguide surface is well known in the art. Under ideal conditions, angular discrimination of fluorescence emerging from the edge of the waveguide would be sufficient to separate the different emission signals. In practice, however, various imperfections in the device can cause fluorescence from the fluorophores in solution to be scattered and to emerge from the optical edge at angles which are normally associated with evanescently coupled fluorescence, i.e. from surface-bound fluorophores.

We have now surprisingly found that this problem can be overcome, with a significantly improved performance over structures described in EP-A-171148 including the structure depicted in FIG. 1, if the wall of the capillary cell opposite to the reagent-bearing waveguide surface is formed of a material transparent to radiation of the wavelengths involved in the assay, but a layer of opaque or light-absorbing material is applied to one or more external surfaces of the said transparent material, preferably at least to the external surface parallel to the waveguide. The term "opaque layer" will be used hereinafter to mean such a layer of opaque or light-absorbing material.

Thus, according to one aspect of the invention we provide a specifically-reactive sample-collecting and testing device possessing a cavity or cavities each having a dimension small enough to enable sample liquid to be drawn into the cavity by capillary action, one surface of the or each cavity carrying an immobilized reagent appropriate to the test to be carried out in the device, said surface being a surface of a first transparent solid plate adapted to act as a light-transmissive waveguide, said plate having an edge which is substantially optically smooth and transverse to the plane of the plate, said device being characterised in that the wall of the or each cavity opposite to said waveguide comprises a second transparent plate, the second transparent plate carrying on its surface remote from the cavity a layer of light-absorbing or opaque material.

As mentioned above, the first transparent solid plate has an edge which is transverse to the plane of the plate. The said edge can be at any transverse angle but is most preferably perpendicular.

In an embodiment, the invention also provides a device as described herein for use in the fluoroimmunoassay or luminescent immunoassay of an analyte present in sample liquid, said device comprising a planar capillary cell for the collection and retention of the volume of sample liquid to be tested therein, said capillary cell comprising a pair of flat, parallel plates fixed together with an air space therebetween and sealed along two opposite sides so as to provide fixed opposed inner surfaces defining a capillary cavity with a first aperture at one end thereof to allow ingress of sample liquid in the capillary cavity and a second aperture at the other end thereof to allow egress of air from the capillary cavity as it fills with sample liquid, wherein one of said plates is a light-transmissive waveguide having an optically smooth edge which is transverse to the plane of the waveguide and perpendicular to the sealed sides thereof, said waveguide having bound to at least a portion of its inner surface, so as to be contacted in use by the sample liquid collected within the capillary cavity, an immobilised reagent capable of binding, either directly or indirectly, a labelled ligand, wherein said immobilised reagent and said labelled ligand are appropriate to the test for analyte to be carried out in the device, the labelled ligand being releasably retained within said device so as in use to be contacted by and released into the sample liquid collected therewithin, and wherein the other plate carries on its surface remote from the cavity a layer of light-absorbing or opaque material.

For convenience, the surface of the second transparent plate which carries the layer of light-absorbing or opaque material is referred to herein as the external surface of the said plate, the opposite surface of the plate being referred to herein as the internal surface.

We have found that in some circumstances it may be advantageous if, in addition to the said external surface, part only of the internal surface of the capillary cavity wall, i.e. part only of the internal surface of the second transparent plate, carries light-absorbing or opaque material.

According to a further aspect of the invention we therefore provide a specifically-reactive sample-collecting and testing device possessing a cavity or cavities each having a dimension small enough to enable sample liquid to be drawn into the cavity by capillary action, one surface of the or each cavity carrying an immobilized reagent appropriate to the test to be carried out in the device, said surface being a surface of a first transparent solid plate adapted to act as a light-transmissive waveguide, said plate having an edge which is substantially optically smooth and transverse to the plane of the plate, said device being characterized in that the wall of the or each cavity opposite to said waveguide comprises a second transparent plate, the second transparent plate carrying on its external surface a layer of light-absorbing or opaque material and also carrying on part only of its internal surface a layer of light-absorbing or opaque material.

The devices according to the invention may be manufactured by methods broadly similar to those described in EP-A-171148 but with the additional feature of applying a light-absorbing or opaque layer to the appropriate surface(s) of the device.

According to the present invention we also provide a method of manufacturing specifically-reactive sample-collecting and testing devices as described above comprising the steps of (a) forming an immobilised specifically-reactive coating on the surface of a sheet material which is to provide part of a multiplicity of the devices, (b) forming a light-absorbing or opaque layer on one or more surfaces of an additional structure which together with said coated sheet material provides for each of the multiplicity of devices a cavity of capillary dimension for collecting and retaining by capillarity a volume of sample liquid in contact with the specifically-reactive coating, and (c) separating the sheet material into portions each providing one or a plurality of the sample-collecting and testing devices.

In this process, both the specifically-reactive coating and the external opaque layer can be continuous or divided into a pattern, e.g. of discrete portions, for example as a two-dimensional array of patches. Where such patches are formed, they can be made for example either by firstly forming a continuous coating and then removing portions of it to leave the desired pattern, e.g. the array of discrete portions, or as an array of patches (for example, screen-printed). Where part of the internal surface of the cavity wall is to carry an opaque layer, the relevant opaque layer applied during manufacture will of course be applied as a discontinuous layer.

The specifically-reactive coating may be immobilised on the surface of the cavity either directly or indirectly. For example, when the specifically-reactive coating is an antibody, indirect immobilisation may be effected by means of an anti-species antibody which is itself bound to the said surface. Alternatively, immobilisation may be effected by conjugating an antibody with biotin and complexing with avidin pre-immobilised on the said surface. Direct immobilisation may be effected by activating the said surface by treatment with a suitable reagent (e.g. a silanisation reagent such as aminopropyltrimethoxysilane), to which the antibody can be covalently coupled using an appropriate crosslinking reagent (e.g. glutaraldehyde).

As already mentioned with reference to devices of the prior art, one method of using a device according to the invention in an assay for a ligand in a liquid sample is to arrange for a fluorescent material to become bound to the immobilised reagent to an extent which will vary depending on the assay and the sample material being assayed and then to carry out optical measurement of the resulting bound fluorescent material.

A suitable fluorescent material typically comprises an ancillary reagent, being either a ligand analogue labelled with a fluorophore or a specific binding partner to the ligand under assay labelled with a fluorophore. When carrying out an assay, the fluorescent material may be introduced, in known amount, into the liquid sample prior to introducing the sample into the device. Alternatively, the fluorescent material may be pre-immobilised on a surface within the device in a soluble, releasable form, e.g. by means of a soluble humectant coating. In the latter case, introducing the sample liquid into the device dissolves the soluble humectant coating so that the ancillary reagent becomes dispersed in the sample liquid.

In an embodiment, the invention provides a method as described hereinbefore comprising the steps of:

(a) immobilising a reagent appropriate to the test to be carried out in the device onto portions of the surface of a transparent flat sheet material which is capable of acting as a light-transmissive waveguide and which is to provide a part of a multiplicity of the devices;

(b) forming a light-absorbing or opaque layer on one surface of an additional structure;

(c) either prior to or subsequent to step (b), attaching to said sheet material the said additional structure in parallel, spaced relation thereto so as to provide for each device of the multiplicity of devices a capillary cavity sealed along two opposite sides thereof and containing the immobilised reagent on at least a portion of the inner surface thereof, said capillary cavity being adapted for collecting and retaining by capillarity a volume of sample liquid in contact with said immobilised reagent; and (d) separating the assembled sheets into portions, each portion providing one or a plurality of the sample collecting and testing devices, such that the transparent sheet material of each device has at least one optically smooth edge transverse to the plane of the sheet and perpendicular to the sealed sides thereof.

The term "ligand analogue" as used herein refers to a species capable of complexing with the same binding site of the same specific binding partner as the ligand under assay, and includes inter alia within its scope a known quantity of the ligand under assay.

Suitable materials for the opaque layer defined hereinbefore are, for example, black paint, optionally curable by heat or infrared radiation, silicone paint, dyes, or any other (preferably inert) material with suitable optical and other physical properties. Such materials should attenuate or absorb light at least at the wavelengths involved in the assay. The thickness of the opaque layer of material will typically be a minimum of 3 microns.

The invention is particularly described herein with reference to fluorescence but it will be understood that analogous considerations apply to phosphorescence and luminescence.

BRIEF DESCRIPTION OF THE FIGURES

For a better understanding of the present invention, reference is made to the accompanying drawings wherein:

Referring to FIG. 1, the device depicted comprises an upper transparent (e.g. plastics, silica or glass) plate 1 and a lower transparent plate 2, both plates being around 1 mm thick fixed together in substantially parallel relation, less than 1 mm apart, by means of bonding tracks (not shown) of suitable adhesive. The cell cavity 3 so formed is open to the outside at both ends, so that when liquid sample is drawn into one opening of the cavity by means of capillarity, air may escape through the other opening. The lower plate 2 of the device is larger than plate 1, the former having a section 4 which extends away from the aperture. In use, section 4 of plate 2 acts as a retentive platform onto which a drop of sample liquid can be applied, so that this liquid can be made to fill the cell cavity 3 by capillary flow.

Immobilised on the inner surface of the capillary cell is a layer 5 of material relevant to the test for which the device is to be employed. In FIG. 1, the layer 5 is a patch of material carried on plate 2. In the case of an immunoassay, the layer 5 may be for example a relevant immobilised antibody. More than one such layer may be present, either in superimposed or adjacent relationship.

Carried on plate 1 on the inner surface of the cell is a layer 6 of light-absorbing or opaque material, the material being appropriate to the nature of the test for which the device is intended to be used and the wavelengths of light intended to be employed.

Figure 1:
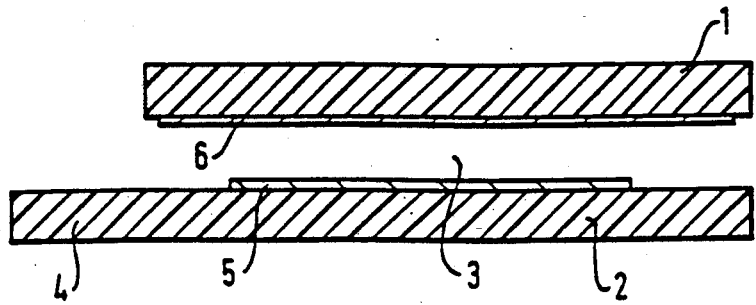
FIG. 1 shows a diagrammatic section through a variant of a capillary fill device suggested in EP-A-171148.
Figure 2:
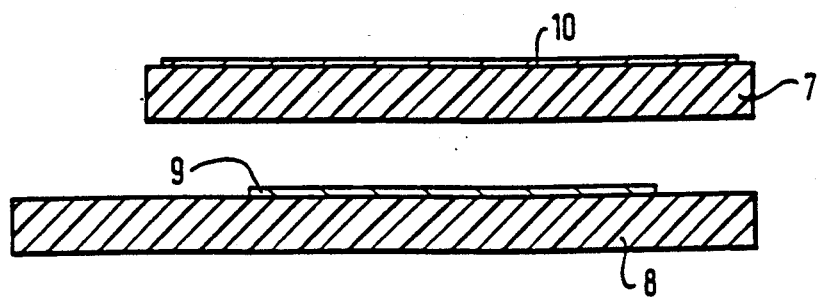
FIGS. 2 to 6 show diagrammatic sections through capillary fill devices according to different embodiments of the present invention.

FIG. 2 shows a diagrammatic section through a capillary cell device according to an embodiment of the present invention. The device comprises an upper transparent plate 7 and a lower transparent plate 8 related as in FIG. 1. A reactive layer 9 is present on the surface of the plate 8. The plate 7 carries on the external surface thereof an opaque layer 10.

Figure 3:
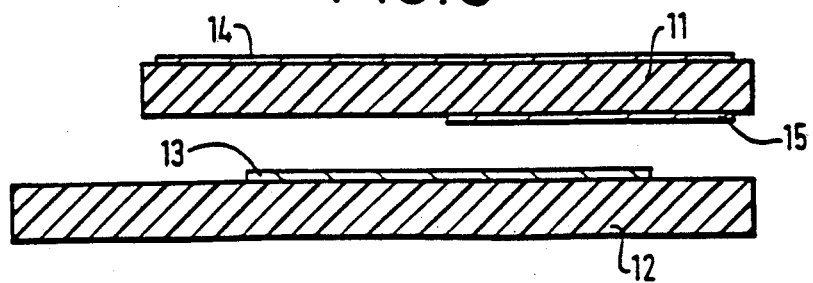

FIG. 3 shows a diagrammatic section through a capillary cell device according to a further embodiment of the present invention. The plates 11 and 12 are present in the same relation as in FIGS. 1 and 2; the reactive layer 13 may be disposed as before. In this embodiment, plate 11 carries an opaque layer 14 on its outside surface and a layer 15 of similar or identical material on part only of its opposite surface (i.e. on the inner surface of the cell cavity).

Figure 4:
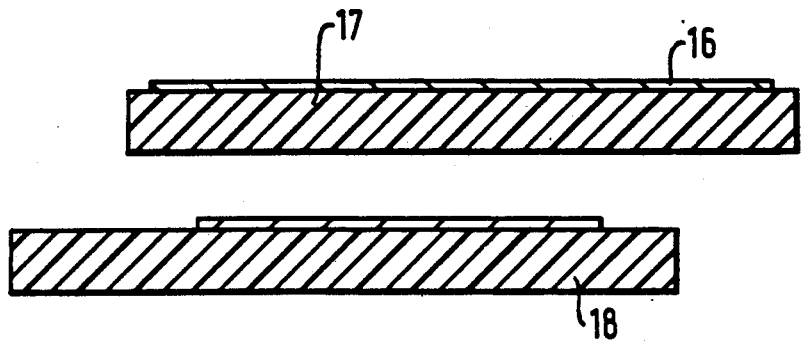

FIG. 4 shows a diagrammatic section through a capillary cell device according to a further embodiment of the present invention. An opaque layer 16 is disposed on the outside surface of the upper plate 17, as for the embodiment shown in FIG. 2. In the embodiment shown in FIG. 4, however, the upper and lower plates 17 and 18 are offset so that each plate has a section which may act as a retentive platform, analogous to the section 4 shown in FIG. 1.

Figure 5:
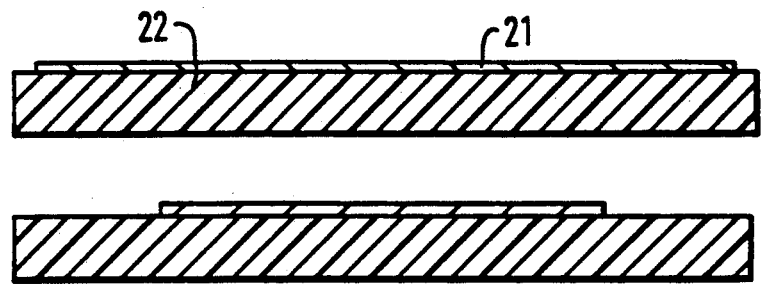

FIG. 5 shows a diagrammatic section through a capillary cell device according to another embodiment of the present invention. Again, an opaque layer 21 is disposed on the outside surface of the upper plate 22. In this case, however, the ends of the upper and lower plates are aligned such that there is no retentive platform.

Figure 6:
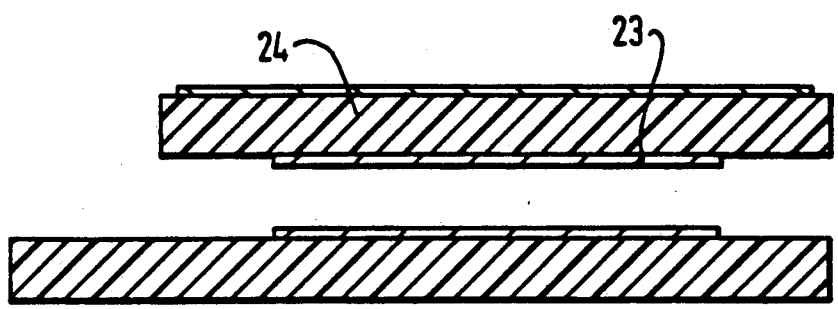

FIG. 6 shows a diagrammatic section through a capillary cell device according to another embodiment of the invention. This embodiment is a variant of that shown in FIG. 2, having as an additional feature a layer 23 of soluble humectant material containing a suitable fluorescent material on the internal surface of the upper transparent plate 24.

Figure 7:
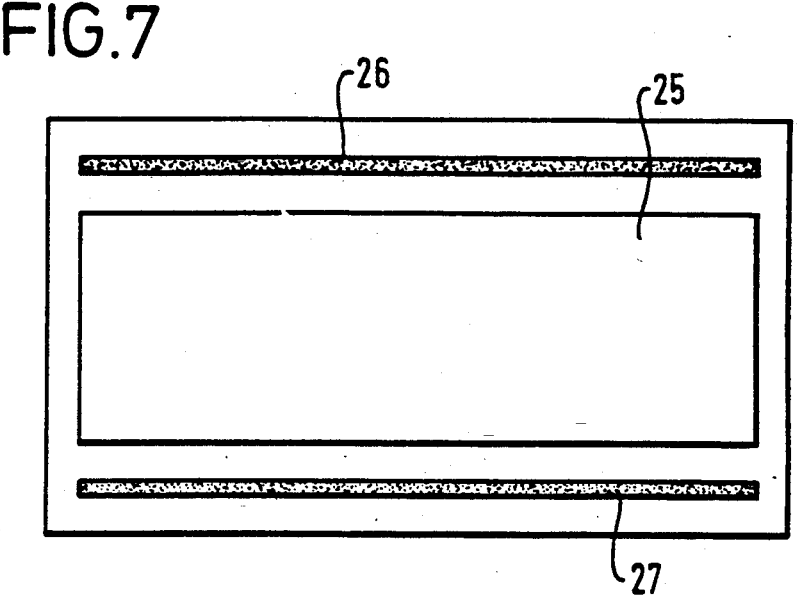
FIG. 7 shows a plan view of the capillary fill device of the invention shown as a section in FIG. 5.

FIG. 7 shows a plan view of the device shown in FIG. 5. The opaque layer 25 is shown as the central region. The upper plate and lower plate are held in the desired relative positions by means of bonding tracks 26 and 27 of a suitable adhesive incorporating glass ballotini of suitable diameter to produce a gap of capillary dimension (e.g. 100 microns).

Figure 8:
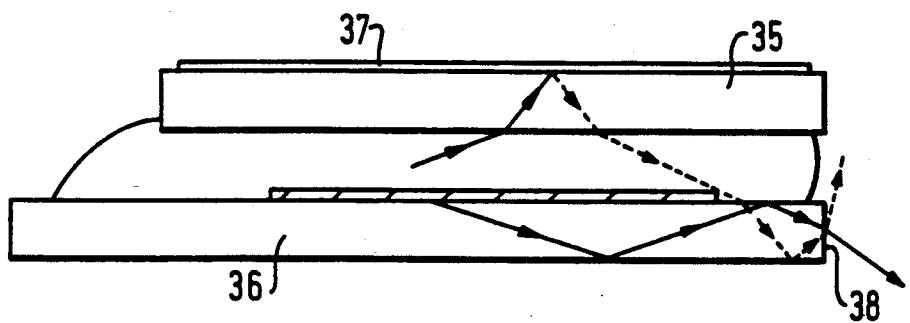
FIG. 8 shows in schematic form attenuation of solution fluorescence in the device of FIG. 2.

FIG. 8 shows schematically the paths followed by a typical ray of fluorescent light arising from a fluorophore in solution and by a typical ray of fluorescent light arising from a surface-bound fluorophore in a device of the present invention according to FIG. 2. Refraction at the sample/glass interface causes certain rays of light emitted from solution fluorophores to propagate in the upper plate 35 at angles to the normal at the interface which are smaller than the critical angle for the interface (for a sample solution/glass interface, these angles would typically lie in the range 0° to 60° to the normal). These rays undergo attenuation on interaction with the opaque layer 37. Fluorescent molecules bound to the reagent immobilised on the surface of the lower glass plate 36 (i.e. within the evanescent field) emit light into the lower plate 36 over the whole range of angles (i.e. including angles to the normal which are greater than the critical angle at the interface of the sample and the lower plate) as a result of evanescent wave coupling. Some of these rays are "guided" through the lower plate, and will emerge from the end 38 without having interacted with the opaque layer 37. The discrimination between fluorescence arising from surface-bound fluorophores and from solution fluorophores is thereby markedly enhanced.

Figure 9:
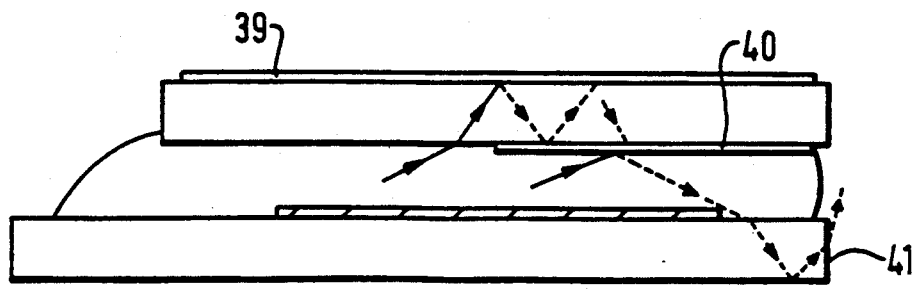
FIG. 9 shows in schematic form attenuation of solution fluorescence in the device of FIG. 3.

FIG. 9 shows schematically the paths of fluorescent light rays arising from solution fluorophores in the device of FIG. 3. In this situation, some of the rays of light resulting from solution fluorescence undergo not only attentuation at opaque layer 39, but further attenuation at opaque layer 40, and so on as a result of partial reflection. Rays interacting with both layers 39 and 40 cannot emerge from end 41 and so use of layer 40 may lead to yet further discrimination between fluorescence arising from surface-bound fluorophores and that from solution fluorophores, and so increase sensitivity.

Figure 10:
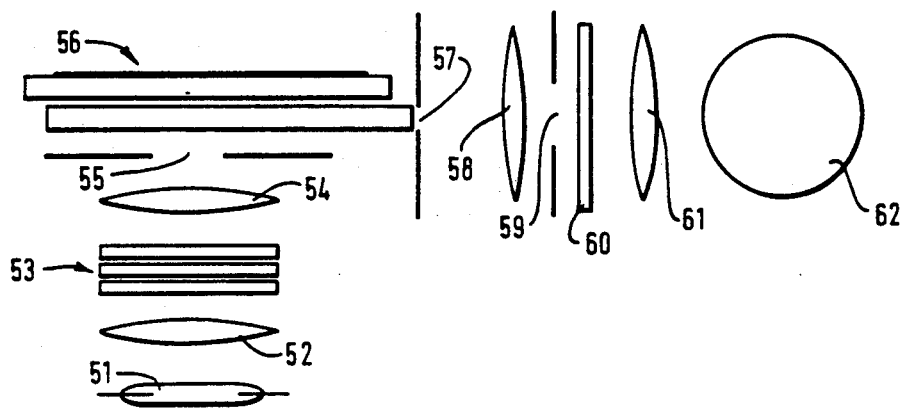
FIG. 10 shows schematically a simple apparatus suitable for carrying out an assay in accordance with the invention.

FIG. 10 shows in schematic form a simple fluorimetry apparatus suitable for use in connection with the present invention. Specific examples of the various components are given hereinafter in Comparative Example A.

Light from a suitable source 51 is roughly collimated by a lens 52 before passing through a filter stack 53, which defines the range of wavelengths used to excite fluorophores taking part in the assay. A further lens 54 focuses this light onto the desired region of the test device 56 through an aperture 55.

Light emerging from a suitable edge of the test device 56 (the "emitted light") passes through an aperture 57 and then through one or more lenses 58. A further aperture 59 is used to define the angular range over which the emitted light is monitored. A further filter 60 is used to remove light of certain wavelengths (e.g. light of excitation wavelengths) and another lens 61 focuses the remaining emitted light onto a photodetector 62.

The invention also provides a method of assaying for a ligand in a sample using a device according to the invention, said method comprising:

(a) incubating the sample in contact with the surface of a waveguide, said waveguide being part of said device wherein the immobilised reagent adsorbed thereon or bound thereto, either directly or indirectly, is a specific binding partner for the ligand it is desired to detect, such that during incubation an ancillary reagent (being either a ligand analogue labelled with a fluorophore or a further specific binding partner labelled with a fluorophore) becomes bound, either directly or indirectly, to the surface of said waveguide;

(b) irradiating said device with light from a suitable light source such that ancillary reagent present in the sample liquid and ancillary reagent bound to the waveguide become excited; and (c) monitoring the radiation emerging from said waveguide in order to determine whether and, if desired, the extent to which ancillary reagent has become bound to said waveguide due to complex formation.

When, in the method of assay according to the invention, the device used is an embodiment the second transparent plate of which carries a layer of light-absorbing or opaque material on both its external surface and part only of its internal surface, the part of the internal surface of the said second plate not carrying light-absorbing or opaque material will be the part which lies opposite the area of the first plate which is irradiated with light from the light source.

The method of the invention is particularly applicable to assays of antigens or antibodies, i.e. to immunoassays, and in a preferred embodiment of the invention the ligand is an antigen and the specific binding partner comprises an antibody to the said antigen. However, the invention is not to be taken as limited to assays of antibodies or antigens. Examples of ligands which may be assayed by the method of the invention are given in Table 1 below, together with an indication of a suitable specific binding partner in each instance.

TABLE 1

| Ligand | Specific Binding Partner |
| --- | --- |
| antigen | specific antibody |
| antibody | antigen |
| hormone | hormone receptor |
| hormone receptor | hormone |
| polynucleotide strand | complementary polynucleotide strand |
| avidin | biotin |

TABLE 1-continued

| Ligand | Specific Binding Partner |
| --- | --- |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used to assay: hormones, including peptide hormones (e.g. thyroid stimulating hormone (TSH), luteinising hormone (LH), human chorionic gonadotrophin (hCG), follicle stimulating hormone (FSH), insulin and prolactin) or non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and alphafetoprotein (AFP)), drugs (e.g. digoxin), sugars, toxins, vitamins, proteins, viruses such as influenza, para-influenza, adeno-, hepatitis, respiratory and AIDS viruses, or microorganisms.

It will be understood that the term "antibody" used herein includes within its scope:

(a) any of the various classes or sub-classes of immunoglobulin, e.g. IgG, IgA, IgM, or IgE derived from any of the animals conventionally used, e.g. sheep, rabbits, oats or mice, (b) monoclonal antibodies, (c) intact molecules or "fragments" of antibodies, monoclonal or polyclonal, the fragments being those which contain the binding region of the antibody, i.e. fragments devoid of the Fc portion (e.g. Fab, Fab', F(ab')$_2$) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, proteins, bacteria, bacterial fragments, cells, cell fragments and viruses) and haptens which may be rendered antigenic under suitable conditions.

Examples of fluorophores which may be used in the method of assay according to the invention include fluorescein isothiocyanate (FITC), rhodamine isothiocyanate, lucifer yellow, 2,4-dinitrofluorobenzene, phenylisothiocyanate and dansyl chloride, XRITC, TRITC and phycobiliproteins (e.g. allophycocyanin and phycoerythrin).

The present invention further provides apparatus suitable for use in the method of assay according to the invention as hereinbefore described which comprises a source of radiation capable of being arranged such that, in use, it enters a device according to the invention as hereinbefore described at such an angle that both the bound and free fluorophores are excited and means for monitoring the emerging radiation. In a further embodiment, the device can be illuminated via a mask, thereby defining the effective volume of the device in which the binding reaction occurs. The effective volume is the product of the distance between base and top plates of the device and the area of the illumination zone.

COMPARATIVE EXAMPLE A

An Optical Immunoassay for Human Chorionic Gonadotrophin (hCG) Carried Out Using a Cell With No Opaque Layer Preparation of Starting Materials (i) Fabrication of antibody-coated waveguides A sheet of Permabloc glass (Pilkington Glass Ltd., St Helens, UK) having a thickness of 1 mm was cleaned with detergent (e.g. Tween 20) in ultra-pure water with ultrasonic agitation. The surface of the glass was activated by incubating it in a 2% solution of aminopropyltriethoxysilane in water at a pH of 3 to 4 for two hours at 25° C. After rinsing in water, the glass sheet was dried at 115° C. for more than four hours. The glass was then incubated for 60 minutes in a 2.5% solution of glutaraldehyde in a 0.05M phosphate buffer (pH 7), and then washed thoroughly with distilled water. The glass was incubated for two to four hours in a 1 percent solution of a monoclonal antibody against hCG in phosphate buffer. The glass sheet was then washed with buffer solution. Unwanted adsorbed protein was removed by soaking with a 6M urea solution in known manner.

(ii) Fabrication of Test Devices

Test devices such as have been described in EP-A-171148 were fabricated by screen printing onto the waveguide baseplate resulting from step (i) bonding tracks of an ultraviolet curing glue (UVS 91, Norland Inc., USA) containing glass microspheres of diameter 100 microns (Jencons Ltd., UK) in a pattern defining the long edges of the capillary cell devices. A clear sheet of Permabloc glass was then placed over the waveguide baseplate, and a vacuum applied to the laminate. As result of the vacuum, the upper sheet of glass was caused to press down onto the glue, the glass microspheres defining a gap of 100 microns between the glass sheets. The laminate was then exposed to an ultraviolet light source in order to cure the glue. Finally, the laminate sheet was broken up into individual test devices using a standard glass scribing and breaking technique.

(iii) Preparation of anti-hCG antibody conjugated to fluorescein isothiocyanate (FITC)

200 mg of FITC (Sigma Chemical Company Ltd., UK) and 5 mg of a second monoclonal antibody to hCG specific for a different antigenic determinant were mixed together in 1.4 ml of 0.2M sodium bicarbonate buffer solution (pH 9.0). The mixture was left for 18 hours at room temperature, during which conjugation of FITC to the monoclonal antibody occurred. The mixture was then purified by gel filtration on Sephadex G-50 superfine.

(iv) Preparation of hCG standard solutions

A freeze-dried preparation of hCG calibrated against the first international reference preparation (75/537) was obtained from Biodata SpA, Milan, Italy. This sample was diluted in horse serum (Serono Diagnostics Ltd., Woking, UK) to give the range of hCG standards required.

(v) Apparatus used in the measurement of the hCG assay

FIG. 10 shows a simple fluorimetry apparatus which was used to make suitable assay measurements. Light from a xenon flash lamp 51 (Heinmann) is roughly collimated by a lens 52 before passing through a filter stack 53 which defines the wavelength range used to excite the FITC-labelled antibodies. The filter stack comprises three filters: A BG7 Schott glass filter (Ealing Electro Optics UK Ltd., Watford, UK) a 450–480 nm FITC bandpass interference filter (Optometrics Ltd., UK) and a 475 nm shortpass interference filter (Comar Instruments Ltd., Cambridge, UK). A second lens 54 focused the excitation light onto the active surface of the test cell 56 through an aperture 55 which defines the illuminated area and hence the active volume of the test cell.

Light emitted from the optical edge of the test cell passes through an aperture 57 which prevents light emitted directly out of the solution from entering the detection optics. A lens system 58 collects the emitted light and an aperture 59 defines the angular range over which the emission is measured. This was chosen to coincide with angles associated with evanescently coupled fluorescence emission. A Schott OG515 515 nm colloidal glass longpass filter 60 (Ealing Electro Optics UK Ltd., Watford, UK) filters out any scattered pump light and a second lens 61 focuses the emission onto a photomultiplier detector 62 (Hamamatsu R931A, Hakuto UK Ltd.).

Assay Procedure for hCG

Figure 11:
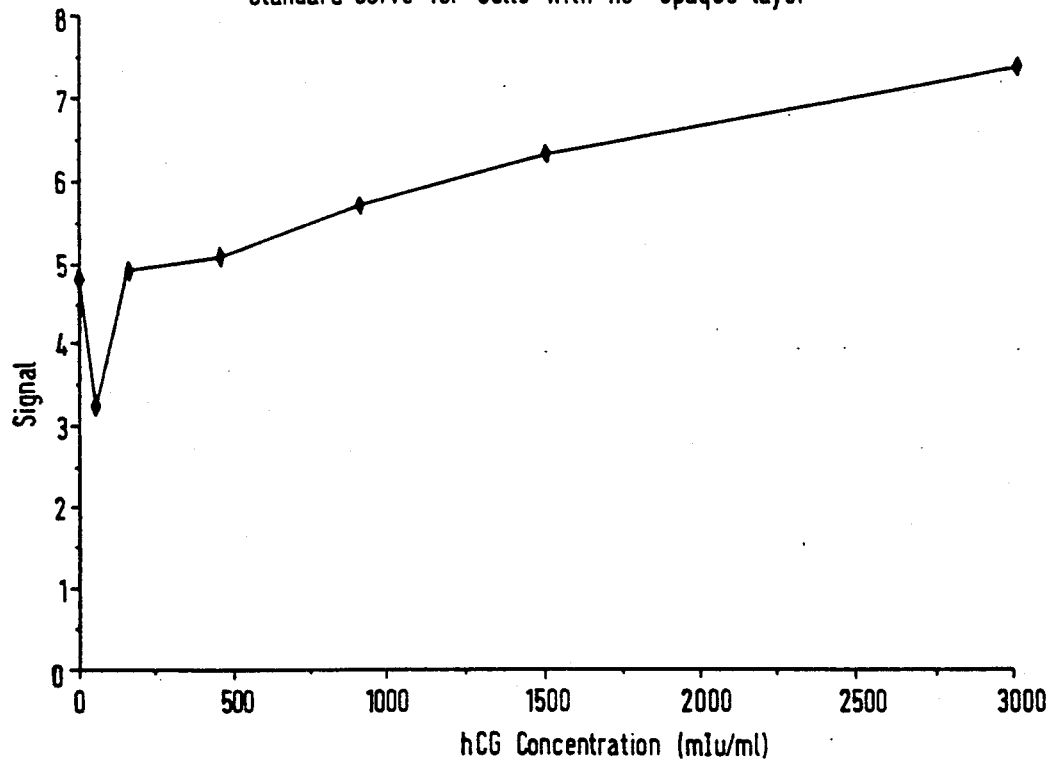
FIG. 11 shows a graph of hCG concentration versus signal for a device having no opaque layer.

The $\alpha$hCG-FITC conjugate was added to each of the hCG standards to give about 0.5 ml of test solution. The conjugate concentration was 1 $\mu$g/ml. Eight test cells were chosen and each was filled with a different test solution. The cells were read after a twenty minute incubation in a humid environment at 20° C. The standard curve thus generated is shown in FIG. 11 for a cell device with no opaque layer. The background signal from 'solution fluorophore' is high, giving rise to a poor signal-to-background ratio which results in poor assay sensitivity.

COMPARATIVE EXAMPLE B

An Optical Immunoassay for hCG Performed in Cells With an Opaque Layer on the Internal Surface of the Device (See FIG. 1)

Preparation of Starting Materials (i) Fabrication of Antibody Coated Waveguides
See Comparative Example A.
(ii) Fabrication of Test Cells Permabloc glass was washed using detergent and ultrasonic agitation. After drying the glass, the desired pattern of opaque layers was screen printed, using black ink, on the surface. After thermally curing the printed opaque material, this sheet of glass was substituted for the untreated Permabloc glass of Comparative Example A taking care to ensure that the opaque material was on the inside of the devices prior to lamination. The remainder of the test cell fabrication process was the same as described in Comparative Example A. Test cells as illustrated in FIG. 1 resulted.

(iii) Preparation of anti-hCG conjugated to FITC
As in Comparative Example A.
(iv) Preparation of hCG Standard Solutions
As in Comparative Example A.
(v) Apparatus used in the measurement of the assay
As in Comparative Example A.

Assay Procedure for hCG

The assay procedure used was identical to that described in Comparative Example A, except that four cells were tested with each of the hCG test solutions.

Figure 12:
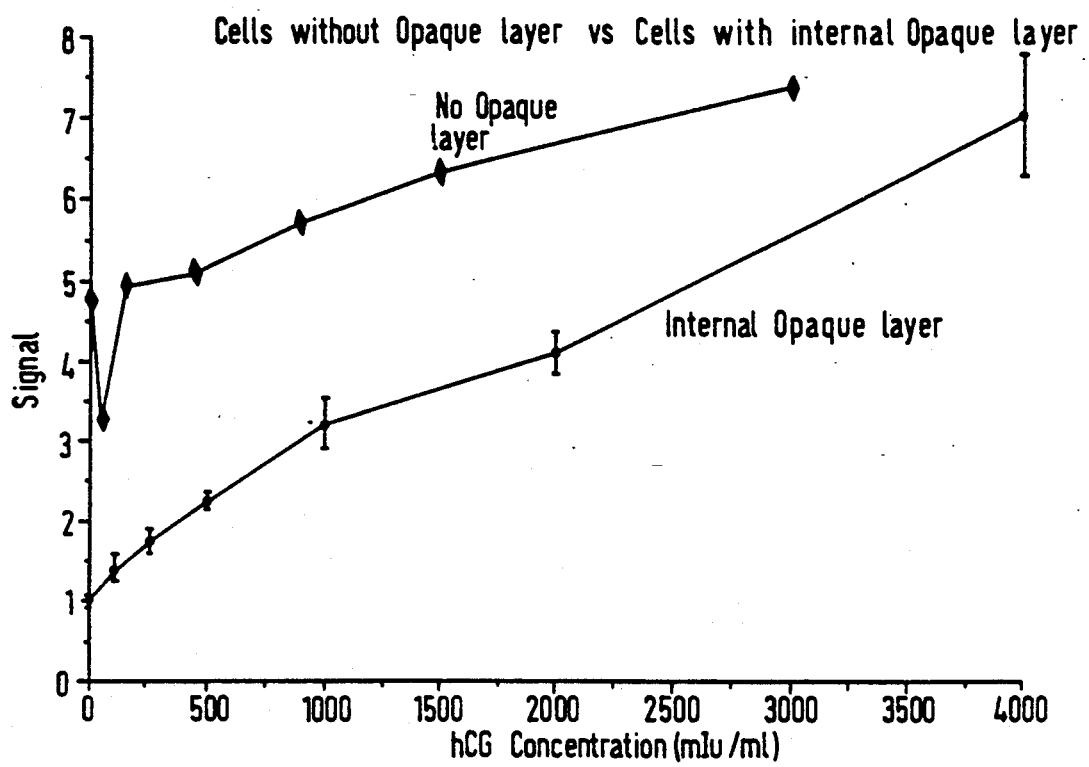
FIG. 12 shows a graph of hCG concentration versus signal comparing a device having no opaque layer with a device having an internal opaque layer.

In FIG. 12 the results of this example are compared to those from Comparative Example A. The presence of an opaque layer has reduced the background signal considerably. As a result there is an improvement in signal-to-background ratio from 1.2:1 to 3:1 for 1000 mIU/mL hCG, therby improving assay sensitivity.

EXAMPLE 1

An Optical Immunoassay for hCG performed in cells with an opaque layer on the external of the device (see FIG. 2)

Preparation of Starting Materials (i) Fabrication of Antibody Coated Waveguides
As in Comparative Example A.
(ii) Fabrication of Test Cells
The method of fabrication of the test cells was the same as in Comparative Example B except that care was taken to ensure that the opaque layers were kept on the outside of the cell during the fabrication process. Test cells illustrated schematically in FIG. 2 resulted.
(iii) Preparation of anti-hCG conjugated FITC
As in Comparative Example A.
(iv) Preparation of hCG Standard Solutions
As in Comparative Example A.
(v) Apparatus used in the measurement of the assay
As in Comparative Example A.

Assay Procedure for hCG

Figure 13:
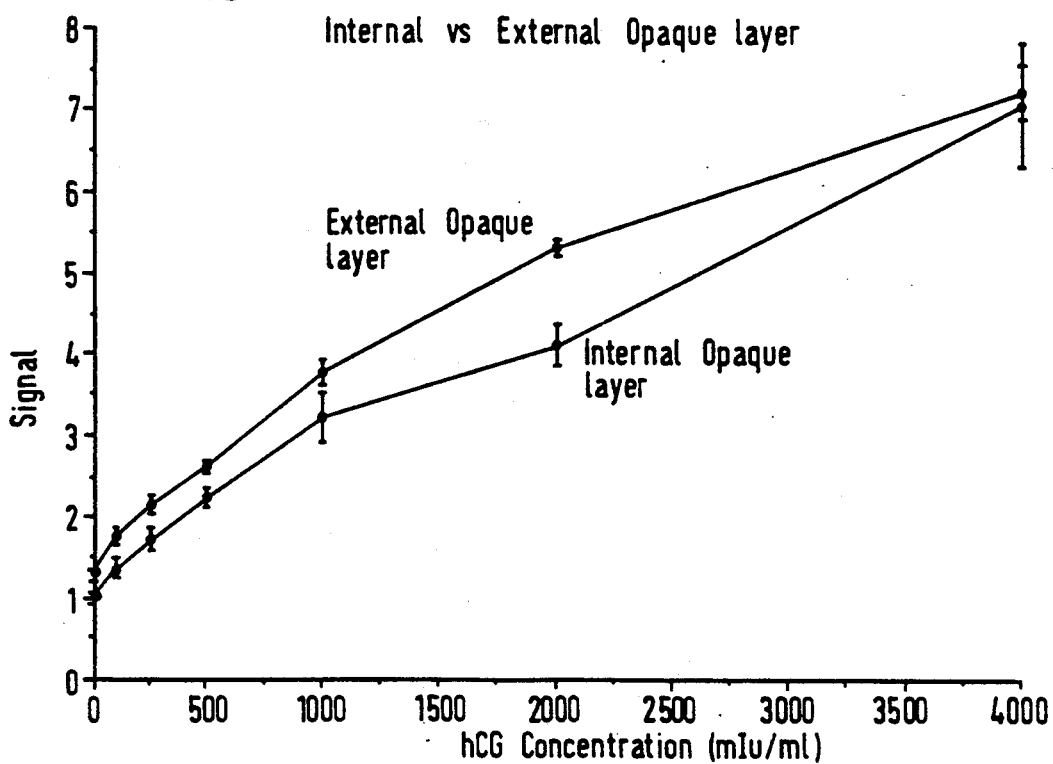
FIG. 13 shows a graph of hCG concentration versus signal comparing a device having an internal opaque layer with a device having an external opaque layer.

As for Comparative Example B. FIG. 13 shows the results from this example and those of Comparative Example B. The standard curves are comparable for each of the cell types. With the opaque layer on the outside of the cell, however, assay precision is increased. (Precision across the curve for the external opaque layer is 4.6% compared with 8.0% for the internal opaque layer; therefore increased assay performance is achieved by this increase in precision). This arises because the cell gap uniformity, and hence sample volume interrogated, is now defined by the glass surface and not the print quality of the opaque layer.

EXAMPLE 2

An Optical Immunoassay for hCG Performed in Cells Possessing Opaque Layers Disposed as in FIG. 3

(i) Fabrication of Antibody Coated Waveguides
As for Comparative Example A.
(ii) Fabrication of Test Cells
A full pattern of opaque material was printed and cured on a sheet of Permabloc glass according to the method described in Comparative Example B. Following this the glass was turned over and a second full pattern was printed on this reverse side in register with the first print. Following curing, half of the second print was removed using a suitable solvent to leave a pattern with half the length but the same width. After cleaning in detergent with ultrasonic agitation a glass laminate was prepared as described in Comparative Example B. Care was taken to ensure that the less extensive print was inside the cell. After curing the glue, the test cells were separated in the usual manner. Test cells illustrated schematically in FIG. 3 resulted.

(iii) Preparation of anti-hCG conjugated FITC
As in Comparative Example A.
(iv) Preparation of hCG Standard Solutions
As in Comparative Example A.
(v) Apparatus used in the measurement of the assay
As in Comparative Example A.

Assay Procedure for hCG

Figure 14:
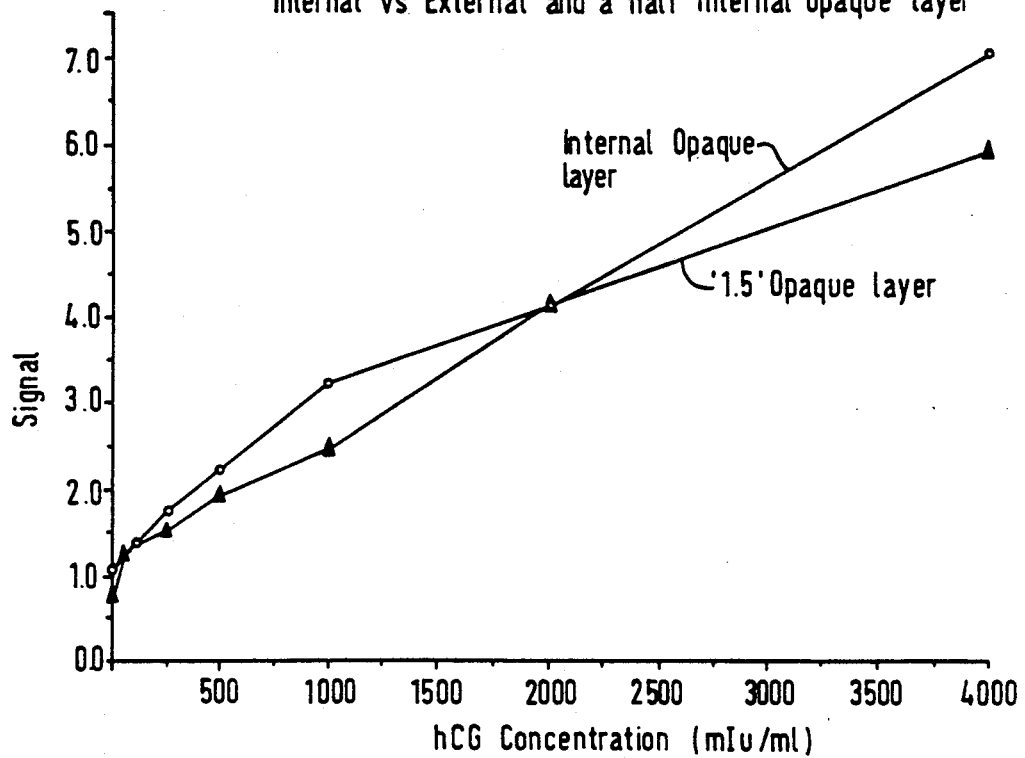
FIG. 14 shows a graph of hCG concentration versus signal comparing a device having an internal opaque layer with a device having an external opaque layer and half an internal opaque layer.

As for Comparative Example B. FIG. 14 shows the result from this example and those of Comparative Example B. The standard curves are again comparable though there is a slight reduction in background signal (from 1.0 to 0.9) over the cells from Comparative Example B. For some cell geometries, e.g. shorter test cells, the greater effectiveness of this arrangement in removing unwanted 'solution signal' could have a more significant effect on assay performance.

EXAMPLE 5

An Optical Immunoassay for hCG Performed on a Cell With Differing Lengths of External Opaque Layers Preparation of Starting Materials (i) Fabrication of Antibody Coated Waveguides
As for Comparative Example A.
(ii) Fabrication of Test Cells
As for Example 1
(iii) Preparation of anti-hCG conjugated FITC
As in Comparative Example A.
(iv) Preparation of Test Solution
A test solution of 1 µg/ml of conjugate in horse serum was used for this example.
(v) Apparatus used in the measurement of the assay
As in Comparative Example A.

Assay Procedure for hCG

A cell was filled with the zero hCG standard test solution and a reading was taken. The opaque layer was reduced in length by 1 mm from the optical edge end using a scalpel and a second reading was taken. This procedure was repeated until no opaque material remained.

Figure 15:
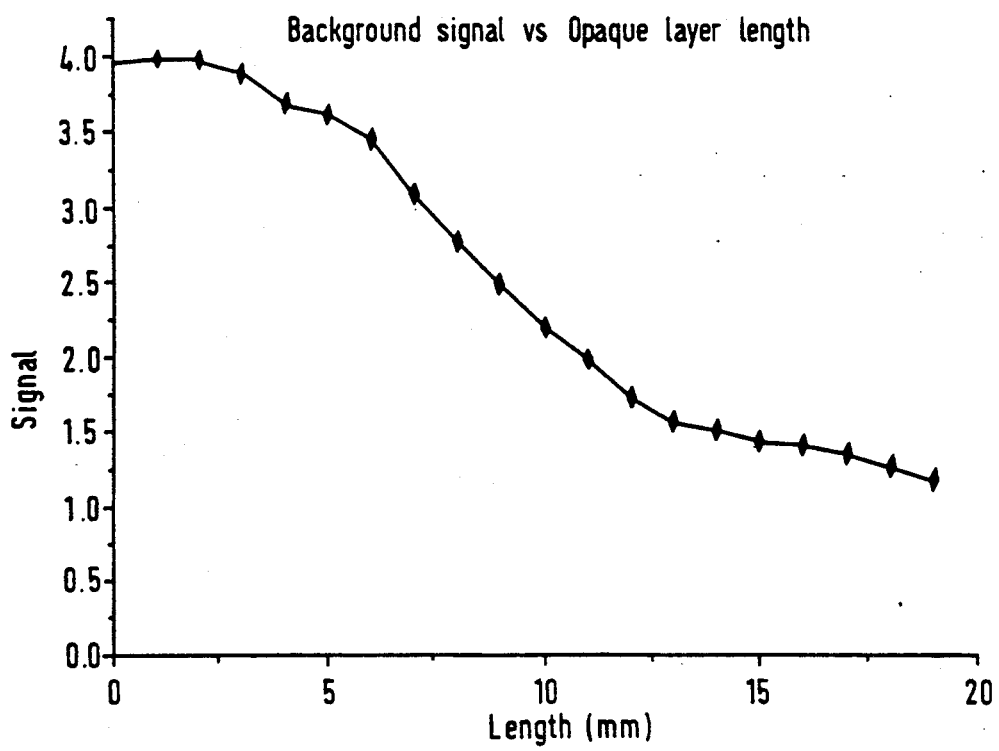
FIG. 15 shows a graph of background signal versus opaque layer length.

In FIG. 15 the typical response as a function of opaque layer length is shown. Opaque layer length is defined as the distance from the rear of the illumination zone to the front edge of the opaque layer in the direction of the optical edge. The results show that for the cell geometry used a length of around 15 mm measured from the edge of the illumination area distal to the optical edge is sufficient to remove effectively the solution signal, decreasing the background signal to a minimum, thereby enhancing the sensitivity of the device (i.e. improving the signal-to-background ratio).

We claim:

1. In a sample collecting and testing device used in an optical assay for analyte present in a sample liquid, said device comprising a pair of parallel transparent plates with a capillary cavity therebetween to allow uptake of sample liquid therein, one of said plates being a light-transmissive waveguide having a reagent appropriate to the assay immobilized on its internal surface, the improvement wherein the other of said plates has an opaque or light-absorbing material coated on its external surface.

2. The device of claim 1 wherein the other of said plates also has an opaque or light-absorbing material coated on part of its internal surface.

3. The device of claim 1 wherein one of said plates has a soluble, releasable form of a fluorophore-labelled reagent appropriate to the assay coated on its internal surface.

4. A device for use in the fluoroimmunoassay or luminescent immunoassay of an analyte present in sample liquid, said device comprising a planar capillary cell for the collection and retention of a volume of sample liquid to be tested therein, said capillary cell comprising a pair of flat, parallel plates fixed together with an air space therebetween and sealed along two opposite sides so as to provide fixed opposed internal surfaces defining a capillary cavity with a first aperture at one end thereof to allow ingress of sample liquid in the capillary cavity and a second aperture at the other end thereof to allow egress of air from the capillary cavity as it fills with sample liquid, wherein one of said plates is a light-transmissive waveguide having an optically smooth edge which is transverse to the plane of the waveguide and perpendicular to the sealed sides thereof, said waveguide having bound to at least a portion of its internal surface, so as to be contacted in use by the sample liquid collected within the capillary cavity, an immobilised reagent capable of binding, either directly or indirectly, a labelled ligand, wherein said immobilised reagent and said labelled ligand are appropriate to the test for analyte to be carried out in the device, the labeled ligand being releasably retained within said device so as in use to be contacted by and released into the sample liquid collected therewithin, and wherein the other of said plates has an opaque or light-absorbing material coated on its external surface.

5. The device of claim 4 wherein the other of said plates also has an opaque or light-absorbing material coated on part of its internal surface.

* * * * *